United States Patent [19]
Berger et al.

[11] 3,962,242
[45] June 8, 1976

[54] 3-(5-NITRO-2-FURYL)-6-CYANO-S-TRIAZOLO(4,3-b)PYRIDAZINE

[75] Inventors: Herbert Berger, Mannheim-Kafertal; Rudi Gall, Grosssachen; Max Thiel; Wolfgang Vömel, both of Mannheim; Winfriede Sauer, Mannheim-Wallstadt, all of Germany

[73] Assignee: Boehringer Mannheim G.m.b.H., Mannheim-Waldhof, Germany

[22] Filed: Jan. 30, 1975

[21] Appl. No.: 545,661

Related U.S. Application Data

[62] Division of Ser. No. 316,197, Dec. 18, 1972.

[30] Foreign Application Priority Data

Jan. 21, 1972 Germany............................ 2202745

[52] U.S. Cl. ........................ 260/250 AC; 424/250
[51] Int. Cl.² ...................................... C07D 237/26
[58] Field of Search ................................ 260/250 A

[56] References Cited
UNITED STATES PATENTS
3,522,256   7/1970   Berger et al.................. 260/250 AC

*Primary Examiner*—Donald G. Daus
*Assistant Examiner*—Anne Marie T. Tighe
*Attorney, Agent, or Firm*—Burgess, Dinklage & Sprung

[57] ABSTRACT

Nitrofuryl-triazolo[4,3-b]pyridazine compounds of the formula

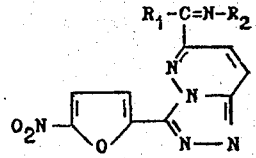

wherein
R₁ is lower alkoxy radical or a saturated 5- or 6-membered heterocyclic ring attached via a cyclic nitrogen atom, which heterocyclic ring can also contain, in addition to said cyclic nitrogen atom, a cyclic oxygen atom or an optionally lower alkylated cyclic nitrogen atom and R₂ is a hydrogen atom or R₁ and R₂ together represent an additional valency bond, are outstandingly effective as bacteriostats and are particularly useful in the treatment of bacterial infections in the urinary tract.

1 Claim, No Drawings

3-(5-NITRO-2-FURYL)-6-CYANO-S-TRIAZOLO(4,3-B)PYRIDAZINE

This is a division of application Ser. No. 316,197, filed Dec. 18, 1972.

The present invention is concerned with new nitrofuryl-triazolo[4,3-b]pyridazine compounds and with bacteriostatic compositions containing them.

The new nitrofuryl-triazolo[4,3-b]pyridazine compounds of the present invention are of the formula:

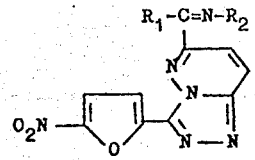

(I)

wherein $R_1$ is lower alkoxy radical (of, e.g., up to 6 carbon atoms) or a saturated 5- or 6-membered heterocyclic ring attached via a cyclic nitrogen atom, which heterocyclic ring can also contain, in addition to said cyclic nitrogen atom, a cyclic oxygen atom or an optionally lower ($C_1$ to $C_6$) alkylated cyclic nitrogen atom and $R_2$ is a hydrogen atom or $R_1$ and $R_2$ together represent an additional valency bond (between the carbon and nitrogen atoms to which they are attached).

We have found that the new compounds (I) according to the present invention possess a surprisingly high antibacterial activity in urine and are, therefore, particularly suitable for the treatment of infections of the urinary tract. In vitro and in vivo, the new compounds (I) show, in some cases, inhibiting activities, especially against *Escherichia coli, Staphylococcus aureus, Pseudomonas aeruginosa* and *Proteus mirabilis*, which are so much better than the most effective urinary antiseptic which is commercially available, i.e., nitrofurantoin, that they represent a valuable addition for medical practice, especially for combating dangerous chronic infections of the urinary tract, such as pyelonephritis.

The new compounds (I) according to the present invention can be prepared, for example, by one of the following methods:

1a. Dehydration of the amide of the formula:

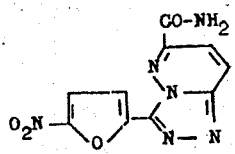

(II)

b. reaction of a compound of the general formula:

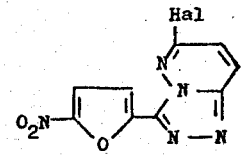

(III)

wherein Hal is a halogen atom, with a cyanide, or c. oxidative cyclisation of 6-cyano-3-[2-(5-nitro-2-furfurylidene)-hydrazino]pyridazone; or d. treatment of N-(6-cyano-3-pyridazonylamino)-(5-nitro-2-furamidine) with an agent splitting off ammonia; whereafter the nitrile obtained of general formula (I), in which $R_1$ and $R_2$ together represent an additional valency bond, is, if desired, reacted with a lower alcohol in the presence of gaseous hydrogen chloride and the salt obtained of the imido ether of the general formula:

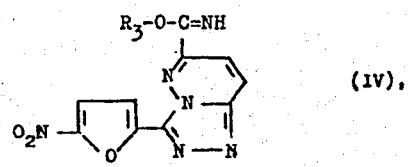

(IV), wherein $R_3$ is a lower alkyl radical, is, if desired, subsequently reacted with an appropriate heterocyclic amine.

2. Nitration of a compound of the general formula:

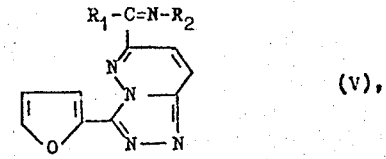

(V), wherein $R_1$ and $R_2$ have the same meanings as above.

The amide of formula (II) can be obtained, for example, by the oxidative cyclisation of 6-carboxy-3-[2-(5-nitro-2-furfurylidene)-hydrazino]-pyridazine to give 3-(5-nitro-2-furyl)-6-carboxy-s-triazolo[4,3-b]pyridazine, the carboxyl group of which is subsequently converted into an amido group. The latter reaction step takes most simply via the acid chloride, which is obtained by reaction of the free acid with thionyl chloride or phosphorus oxychloride, but the acid esters or acid imidazolides can also be used.

The oxidative cyclisation of the above-mentioned starting material, as well as of the corresponding 6-cyanopyridazine derivative, can be carried out at a slightly elevated temperature, preferably in trifluoroacetic acid, glacial acetic acid or a mixture thereof. Lead tetraacetate has proved to be particularly useful as oxidation agent.

The dehydration can be carried out in known manner in an inert, hydroxy group-free solvent with the help of phosphorus pentoxide or with phosphorus oxychloride alone.

The compounds (III) can be obtained in the above-described manner by the cyclisation of, for example, 6-chloro-3-[2-nitro-2-furfurylidene)-hydrazino]-pyridazine. The nitrile group can be introduced in manner analogous to the Kolbe nitrile synthesis.

The N-(6-cyano-3-pyridazinylamino)-(5-nitro-furamidine) used as starting material can be prepared by the condensation of 5-nitro-2-furan-imido ether with 6-cyano-3-hydrazino-pyridazine. The cyclisation according to the present invention can be brought about simply by heating in an inert solvent. However, the splitting off of ammonia also takes place with the use of aqueous mineral acids at ambient temperature or possibly with warming.

The corresponding nitrile is then first converted into the corresponding imido ether hydrochloride (IV), for example, by means of alcoholic hydrochloric acid at a low temperature in a hydroxyl group-free solvent, for example nitrobenzene, to which some ether has been added, which imido ether hydrochloride, after neutralization with an aqueous solution of sodium bicarbonate, can then be reacted at an elevated temperature with an appropriate heterocyclic amine in a polar organic solvent, for example dioxan.

The nitration of the compounds of general formula (V) can be carried out in the usual manner, for example, with nitric acid in acetic anhydride in the cold. The starting materials (V) can be obtained, for example, by the cyclisation of 6-cyano-3-(2-furfurylidene-hydrazino)-pyridazine and reaction of the carboxylic acid nitrile obtained therefrom in manner analogous to process 1d) above.

The following Examples illustrate the preparation of the compounds of the present invention:

EXAMPLE 1

Preparation of
3-(5-Nitro-2-furyl)-6-cyano-s-triazolo[4,3-b]pyridazine 230 g. 3-chloro-6-cyano-pyridazine were suspended in 2500 ml. ethanol and 198 ml. hydrazine hydrate were added at ambient temperature, with cooling. The reaction mixture was then stirred for 30 minutes at ambient temperature and the precipitated crystals were filtered off with suction, washed with ethanol, triturated with a little ice water, filtered off with suction and washed with ice water. There were thus obtained 195 g. crude 3-hydrazino-6-cyano-pyridazine; m.p. 186°–192°C.

19.5 g. 3-hydrazino-6-cyano-pyridazine were dissolved in 365 ml. water and 192 ml. methanol, with heating. At 50°C., there were added 20 ml. 2N hydrochloric acid and a solution of 22.3 g. 5-nitrofuran-2-aldehyde in 192 ml. methanol, whereafter the reaction mixture was stirred for 15 minutes at this temperature and then for 30 minutes at ambient temperature. The solid material was then filtered off with suction and washed with 50% aqueous methanol and thereafter with ether. There were thus obtained 35.17 g. crude 6-cyano-3-[2-(5-nitro-2-furfurylidene)-hydrazino]-pyridazine, which was boiled for 15 minutes with 220 ml. dioxan. After filtering off with suction at 50°C., there were obtained 23.6 g. of the pure compound, which melts, with decomposition, at 275°–278°C.

23.6 g. 6-cyano-3-[2-(5-nitro-2-furfurylidene)-hydrazino]-pyridazine (m.p. 275°–278°C. (decomp.)) were dissolved in 320 ml. hot trifluoroacetic acid, diluted with 320 ml. glacial acetic acid and 46.5 g. lead tetraacetate were added portionwise, with stirring, at a temperature between 45°C. and 50°C., thereafter stirred for 30 minutes at 50°C. and the small amount of insoluble material quickly filtered off with suction. The filtrate was gently evaporated in a vacuum and the evaporation residue is triturated with ice water. There were thus obtained 19.7 g. crude 3-(5-nitro-2-furyl)-6-cyano-s-triazolo[4,3-b]-pyridazine; m.p. 186°–190°–198°C. After recrystallization from isopropanol-dioxan (1:1), with the addition of charcoal, the compound melts, with decomposition, at 212°–214°C.

EXAMPLE 2

Preparation of
3-(5-Nitro-2-furyl-s-triazolo[4,3-b]-pyridazine-6-carboximic acid ethyl ester 1.28 g. 3-(5-nitro-2-furyl)-6-cyano-s-triazolo-[4,3-b]pyridazine were dissolved in 20 ml. warm nitrobenzene, mixed at ambient temperature with 0.3 ml. ethanol and 5 ml. ether and dry hydrogen chloride gas passed through for 1 hour at a temperature of 0°–5°C., whereafter the reaction mixture was left to stand overnight in a refrigerator, with the exclusion of moisture and the reaction product subsequently precipitated out by the addition of 150 ml. ether. It was then filtered off with suction and quickly washed with ether. The crude hydrochloride of the imido ether obtained was then introduced portionwise into a saturated and cooled aqueous solution of bicarbonate, whereby, after filtering off with the suction and drying, there were obtained 0.95 g. of the crude imido ether. By means of recrystallization from 12 ml. dioxan, with the addition of charcoal, there were obtained 0.47 g. 3-(5-nitro-2-furyl)-s-triazolo[4,3-b]pyridazine-6-carboximic acid ethyl ester (m.p. 196°–198°C.), which contains about 0.5 mole equivalent of dioxan.

EXAMPLE 3

Preparation of
3-(5-nitro-2-furyl)-s-triazolo[4,3-b]pyridazine-6-carboximic acid morpholide 0.9 g. crude 3-(5-nitro-2-furyl)-s-triazolo[4,3-b]-pyridazine-6-carboximic acid ethyl ester was dissolved in 120 ml. dioxan, mixed with 1.3 g. morpholine and boiled under reflux for 1.5 hours. Thereafter, the reaction mixture was cooled for 2 hours in an ice bath and the precipitated crystals were filtered off with suction and washed with dioxan and ether. There was obtained 0.45 g. olive-yellow 3-(5-nitro-2-furyl)-s-triazolo[4,3-b]pyridazine-6-carboximic acid morpholide; m.p. 232°–234°C. (decomp.).

In an analogous manner, from 3-(5-nitro-2-furyl)-s-triazolo[4,3-b]pyridazine-6-carboximic acid ethyl ester there were obtained:

with pyrrolidine: 3-(5-nitro-2-furyl)-s-triazolo[4,3-b]-pyridazine-6-carboximic acid pyrrolidide;
with piperidine: 3-(5-nitro-2-furyl)-s-triazolo[4,3-b]-pyridazine-6-carboximic acid piperidide; and
with 4-methyl-piperazine: 3-(5-nitro-2-furyl)-s-triazolo[4,3-b]-pyridazine-6-(carboximic acid-4-methyl-piperazide).

The bacteriostatic activity of the compounds in accordance with the invention was evaluated in vitro and in vivo. The following comparison compound and compounds according to the invention were used in the tests:

| Compound No. | Chemical Name |
|---|---|
| A (Comparison Compound) | N-(5-Nitrofuryliden)-1-amino-hydantoine (sold under the trade name "Furadantin" by Norwich Pharmacal Co.) |
| 1 | 3-(5-Nitro-2-furyl)-6-cyano-s-triazolo[4,3-b]pyridazine |
| 2 | 3-(5-Nitro-2-furyl)-s-triazolo[4,3-b]-pyridazine-6-carboximic acid morpholide |
| 3 | 3-(5-Nitro-2-furyl)-s-triazolo[4,3-b]-pyridazine-6-carboximic acid ethyl ester |

The absolute bacteriostatic minimal concentration in vitro of the test compounds, for six different bacterial species, is set out in micrograms of test compound per milliliter in the following Table I.

In addition the compounds were evaluated with respect to their bacteriostatic activity in the excreted urine of rats following oral administration. The results of these experiments are set out in Table II. The bacteriostatic maximum dilution of urine against *Escherichia coli* (106) was determined 22 hours after 20 milligrams of test compound per kilogram of body weight had been orally administered to the rats. Six (nine) rats were employed for each experiment (test compound); the test results are calculated on the basis of 50 (75) milliliter urine samples. Each value reported represents the result of one experiment and is expressed in terms of the volumes of water with which one volume of the excreted urine sample could be diluted and still retain its bacteriostatic property, due to the presence of test compound.

suspension or solution; in the form of solutions in non-aqueous, hygroscopic liquid vehicles such as polyethylene glycol, for instance 0.1–0.5% solutions in polyethylene glycol; incorporation into a water-soluble ointment-like base (concentration 0.1–0.5%) or in a powder base composed for instance of water-soluble polyethylene glycols (concentration 0.1 to 0.5%); or in a form suitable for ingestion. Thus, a preferred form is a tablet containing 50 to 200 mg. of active compound. Depending on the conditions, symptomatic and laboratory responses 100 to 400 mg. per day can be administered. Another preferred form for orally administering the compounds of the invention is in the form of a suspension thereof in a water miscible flavored gel.

TABLE 1

| Compound No. | ABSOLUTE BACTERIOSTATIC ACTIVITY IN VITRO (MINIMAL CONCENTRATION IN μg/ml) | | | | | |
| --- | --- | --- | --- | --- | --- | --- |
| | Streptococcus faecalis(155) | Escherichia coli(18) | Escherichia coli(106) | Proteus mirabilis(298) | Proteus mirabilis(279) | Pseudomonas-aeruginosa(71) |
| A | 16 | 8 | 4 | 256 | 128 | >128 |
| 1 | 2 | 0.5 | 0.125 | 128 | 4 | 16 |
| 2 | 4 | 0.5 | 0.125 | 16 | 8 | 2 |
| 3 | 8 | 1 | 0.25 | 64 | 32 | 64 |

TABLE II

| Compound No. | Maximum Bacteriostatic Dilution (Volume Ratio) |
| --- | --- |
| A | 1:54 |
| | 1:30 |
| | 1:41 |
| | 1:19 |
| | 1:40 |
| | 1:21 |
| 1 | 1:112 |
| | 1:104 |
| | 1:120 |
| 2 | 1:59 |
| | 1:62 |
| | 1:80 |
| | 1:364 |
| 3 | 1:50 |
| | 1:46 |

The compounds of this invention are anti-microbials and have been found to be bactericidal to the pathogens found in surface infections, gram negative as well as gram positive. They additionally have utility as agents for routine treatment of acute and chronic bacterial infections of the urinary tract, including those caused by Proteus ap. Further they lend themselves because of their properties to use in the prevention or treatment of mixed surface infections or wounds, severe burns, cutaneous ulcers, pyodermas osteomyelitis, preparation of wounds and burns for skin grafting and prevention of infection of grafts and donor sites.

The compounds of the invention can be employed in the form of aqueous solutions or suspensions thereof, as for instance, in the form of an 0.01 to 0.05% aqueous Such gel can contain from 1 to 10 mg of compound per cc.

The compounds (I) can be administered orally and parenterally in admixture with a liquid or solid pharmaceutical diluent or carrier. As an injection medium, it is preferable to use water which contains the stabilizing agents, solubilizing agents and/or buffers conventional for injection solutions. Additives of this type include for example, tartrate and borate buffers, ethanol, dimethyl sulphoxide, complex-forming agents (for example ethylene-diamine-tetraacetic acid) and high molecular weight polymers (for example liquid polyethylene oxide) for viscosity regulation. Solid carrier materials include, for example starch, lactose, mannitol, methylcellulose, talc, highly dispersed silicic acid, high molecular weight fatty acids (for example stearic acid), gelatine, agar-agar, calcium phosphate, magnesium stearate, animal and vegetable fats and solid high molecular weight polymers (for example polyethylene glycols). Compositions suitable for oral administration can, if desired, also contain flavoring and/or sweetening agents. For external use, the compounds (I) according to the present invention can also be used in the form of powders and salves; for this purpose, they are mixed, for example, with powdered, physiologically compatible diluents or with conventional salve bases.

It will be understood that the specification and examples are illustrative but not limitative of the present invention and that other embodiments within the spirit and scope of the invention will suggest themselves to those skilled in the art.

What is claimed is:

1. 3-(5-nitro-2-furyl)-6-cyano-s-triazolo[4,3-b]pyridazine.

\* \* \* \* \*